US00PP19546P2

(12) United States Plant Patent
Smith

(10) Patent No.: US PP19,546 P2
(45) Date of Patent: Dec. 2, 2008

(54) ***CHRYSOCEPHALUM* PLANT NAMED 'SILSUN'**

(50) Latin Name: *Chrysocephalum apiculatum*
Varietal Denomination: Silsun

(76) Inventor: Kim Smith, 1975 South Gippsland Highway, Cranbourne, Victoria, 3977 (AU)

( * ) Notice: Subject to any disclaimer, the term of this patent is extended or adjusted under 35 U.S.C. 154(b) by 0 days.

(21) Appl. No.: 11/999,271

(22) Filed: Dec. 4, 2007

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Kent L Bell
(74) *Attorney, Agent, or Firm*—C. A. Whealy

(57) ABSTRACT

A new and distinct cultivar of *Chrysocephalum* plant named 'Silsun', characterized by its compact, low spreading and mounding plant habit; silvery pubescent leaves and stems; freely flowering habit; large inflorescences positioned above the foliage; bright yellow-colored inflorescences; and good garden performance.

2 Drawing Sheets

Botanical designation: *Chrysocephalum apiculatum.*
Cultivar denomination: 'Silsun'.

BACKGROUND OF THE INVENTION

The present invention relates to a new and distinct cultivar of *Chrysocephalum,* botanically known as *Chrysocephalum apiculatum* and hereinafter referred to by the name 'Silsun'.

The new *Chrysocephalum* originated from an open-pollination in Cranbourne, Victoria, Australia, of an unnamed selection of *Chrysocephalum apiculatum,* not patented, as the female, or seed, parent with an unknown selection of *Chrysocephalum apiculatum* as the male, or pollen, parent. The new *Chrysocephalum* was discovered and selected by the Inventor as a single flowering plant from within the progeny of the stated open-pollination in a controlled environment in Cranbourne, Victoria, Australia in April, 2004.

Asexual reproduction of the new *Chrysocephalum* by vegetative cuttings in a controlled environment in Cranbourne, Victoria, Australia since August, 2004 has shown that the unique features of this new *Chrysocephalum* are stable and reproduced true to type in successive generations.

SUMMARY OF THE INVENTION

The cultivar Silsun has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Silsun'. These characteristics in combination distinguish 'Silsun' as a new and distinct cultivar of *Chrysocephalum:*

1. Compact, low spreading and mounding plant habit.
2. Silvery pubescent leaves and stems.
3. Freely flowering habit.
4. Large inflorescences positioned above the foliage.
5. Bright yellow-colored inflorescences.
6. Good garden performance.

Plants of the new *Chrysosephalum* differ from plants of the female parent selection in the following characteristics:

1. Plants of the new *Chrysocephalum* are more compact than plants of the female parent selection.
2. Plants of the new *Chrysocephalum* have larger inflorescences than plants of the female parent selection.

Plants of the new *Chrysocephalum* can be compared to plants of the *Chrysocephalum* cultivar Golden Buttons, not patented. In side-by-side comparisons conducted in Cranbourne, Victoria, Australia, plants of the new *Chrysocephalum* differed from plants of the cultivar Golden Buttons in the following characteristics:

1. Plants of the new *Chrysocephalum* were more compact, spreading and mounding than plants of the cultivar Golden Buttons.
2. Stems of plants of the new *Chrysocephalum* were thicker, more spreading and pubescent than stems of plants of the cultivar Golden Buttons.
3. Plants of the new *Chrysocephalum* were more freely branching than plants of the cultivar Golden Buttons.
4. Plants of the new *Chrysocephalum* were more freely flowering than plants of the cultivar Golden Buttons.
5. Plants of the new *Chrysocephalum* had larger inflorescences than plants of the cultivar Golden Buttons.
6. Inflorescences of plants of the new *Chrysocephalum* were paler yellow in color than inflorescences of the cultivar Golden Buttons.
7. Plants of the new *Chrysocephalum* had longer and thicker peduncles than plants of the cultivar Golden Buttons.

BRIEF DESCRIPTION OF THE PHOTOGRAPHS

The accompanying colored photographs illustrate the overall appearance of the new *Chrysocephalum,* showing the colors as true as it is reasonably possible to obtain in colored reproductions of this type. Colors in the photographs may differ slightly from the color values cited in the detailed botanical description which accurately describe the colors of the new *Chrysocephalum.*

The photograph on the first sheet comprises a side perspective view of typical flowering plants of 'Silsun' grown in a container.

The photograph on the second sheet is a close-up view of typical inflorescences of 'Silsun'.

DETAILED BOTANICAL DESCRIPTION

The aforementioned photographs and following observations, measurements and values describe plants grown in 20-cm containers in Cranbourne, Victoria, Australia, under commercial practice during the spring and summer in a polyethylene-covered greenhouse with day temperatures ranging from 10° C. to 40° C., night temperatures ranging from 4° C. to 28° C. and light levels ranging from 5,000 lux to 9,000 lux. Plants were pinched at planting and then a second time five weeks later. Plants had been growing for about six months when the photographs and the description were taken. In the following description, color references are made to The Royal Horticultural Society Colour Chart, 1995 Edition, except where general terms of ordinary dictionary significance are used.

Botanical classification: *Chrysocephalum apiculatum* cultivar Silsun.

Parentage:

*Female, or seed, parent.*—Unnamed selection of *Chrysocephalum apiculatum,* not patented.

*Male, or pollen, parent.*—Unknown selection of *Chrysocephalum apiculatum,* not patented.

Propagation:

*Type.*—By vegetative cuttings.

*Time to initiate roots, summer.*—About 7 to 12 days at temperatures of 22° C. to 39° C.

*Time to initiate roots, winter.*—About 12 to 20 days at temperatures of 10° C. to 20° C.

*Time to produce a rooted young plant, summer.*—About 20 to 30 days at temperatures of 16° C. to 39° C.

*Time to produce a rooted young plant, winter.*—About 25 to 45 days at temperatures of 10° C. to 20° C.

*Root description.*—Thin, fibrous; white in color becoming brown with development.

*Rooting habit.*—Moderately dense.

Plant description:

*Plant form/habit.*—Compact, low spreading and mounded plant habit; moderately vigorous growth habit. Freely branching habit with numerous lateral branches developing after pinching.

*Plant height.*—About 30 cm to 50 cm.

*Plant width (spread).*—About 55 cm to 80 cm.

*Lateral branches.*—Diameter: About 6 mm to 9 mm. Internode length: About 1.6 cm to 2.6 cm. Strength: Moderately strong. Texture: Densely pubescent, tomentose. Color: 202D.

Foliage description:

*Arrangement.*—Alternate, simple; sessile.

*Length.*—About 3 cm to 9 cm.

*Width.*—About 0.9 cm to 4.5 cm.

*Shape.*—Narrowly to broadly spatulate.

*Apex.*—Acute.

*Base.*—Clasping.

*Margin.*—Entire.

*Texture, upper and lower surfaces.*—Densely pubescent.

*Venation pattern.*—Pinnate.

*Color.*—Developing leaves, upper surface: 188B to 188C. Developing leaves, lower surface: 188C to 188D. Fully expanded leaves, upper surface: 191A to 191B; venation, 188B to 188C. Fully expanded leaves, lower surface: 191B to 191C; venation, 188B to 188C.

Inflorescence description:

*Appearance.*—Composite inflorescence form with disc florets surrounded by showy involucral bracts. Inflorescences borne above the foliage. Freely flowering habit with about 11 to 25 inflorescences developing per lateral branch.

*Fragrance.*—Faintly fragrant; sweet, honey-like.

*Flowering season.*—Plants flower from spring through autumn in Australia; flowering continuous during this period. Plants begin flowering about seven to twelve weeks after planting.

*Inflorescence longevity.*—Inflorescences last about 8 to 14 weeks on the plant and about two to three weeks as a cut flower. Inflorescences persistent.

*Inflorescence bud.*—Height: About 5 mm to 7 mm. Diameter: About 5 to 7 mm. Shape: Oblate. Color: 13A to 13B.

*Inflorescence size.*—Diameter: About 7.5 cm. Depth (height): About 2.5 cm to 5.5 cm. Diameter of disc: About 8 mm. Receptacle height: About 2.5 mm. Receptacle diameter: About 4 mm.

*Disc florets.*—Arrangement: Massed at center of receptacle. Shape: Filiform to tubular, elongated. Apex: Five-pointed. Length: About 4 mm. Width: About 1 mm. Texture: Smooth, glabrous. Color, immature: 162A. Color, mature: 23A.

*Involucral bracts.*—Number per inflorescence: Numerous arranged in about 9 to 14 whorls. Length: About 2 mm to 3 mm. Width: About 1 mm. Shape: Broadly lanceolate. Apex: Acute. Margin: Toothed or laciniate; towards the apex, entire. Texture, upper and lower surfaces: Smooth, glabrous; satiny. Color, upper surface: 9A to 9B. Color, lower surface: 9B to 9C.

*Peduncles.*—Length, terminal peduncle: About 3 mm to 9 mm. Length, fourth peduncle: About 0.9 cm to 1.8 cm. Length, seventh peduncle: About 1 cm to 1.5 cm. Diameter: About 2 mm. Strength: Moderately strong to strong, flexible. Texture: Densely pubescent. Color: 202D.

*Reproductive organs.*—Present on disc florets only. Androecium: Filament length: Less than 1 mm. Filament color: Close to 155D. Anther length: Less than 1 mm. Anther shape: Club-shaped. Pollen amount: Moderate. Gynoecium: Stigma shape: Bi-lobed. Style length: About 3 mm. Style color: Close to 155D.

*Seeds.*—Seed set is nil to poor on plants of the new *Chrysocephalum.*Quantity per inflorescence: None to about three. Length: Less than 1 mm. Diameter: Less than 1 mm.

Disease/pest resistance: Plants of the new *Chrysocephalum* have not been noted to be resistant to pathogens common to *Chrysocephalum.* Plants of the new *Chrysocephalum* are relartively tolerant to most pests of *Chrysocephalum* with the exception of caterpillars.

Garden performance; Plants of the new *Chrysocephalum* have been observed to have good garden performance and tolerate rain, wind and temperatures ranging from about −3° C. to about 45° C.

It is claimed:

1. A new and distinct *Chrysocephalum* plant named 'Silsun' as illustrated and described.

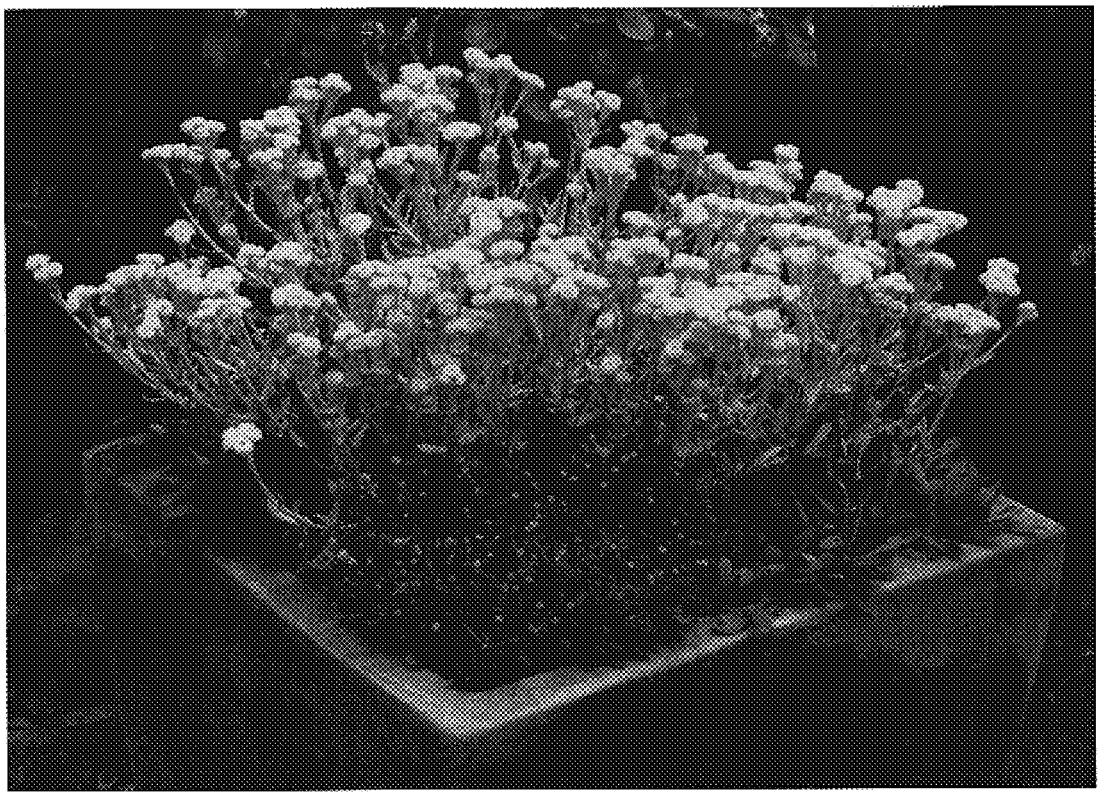

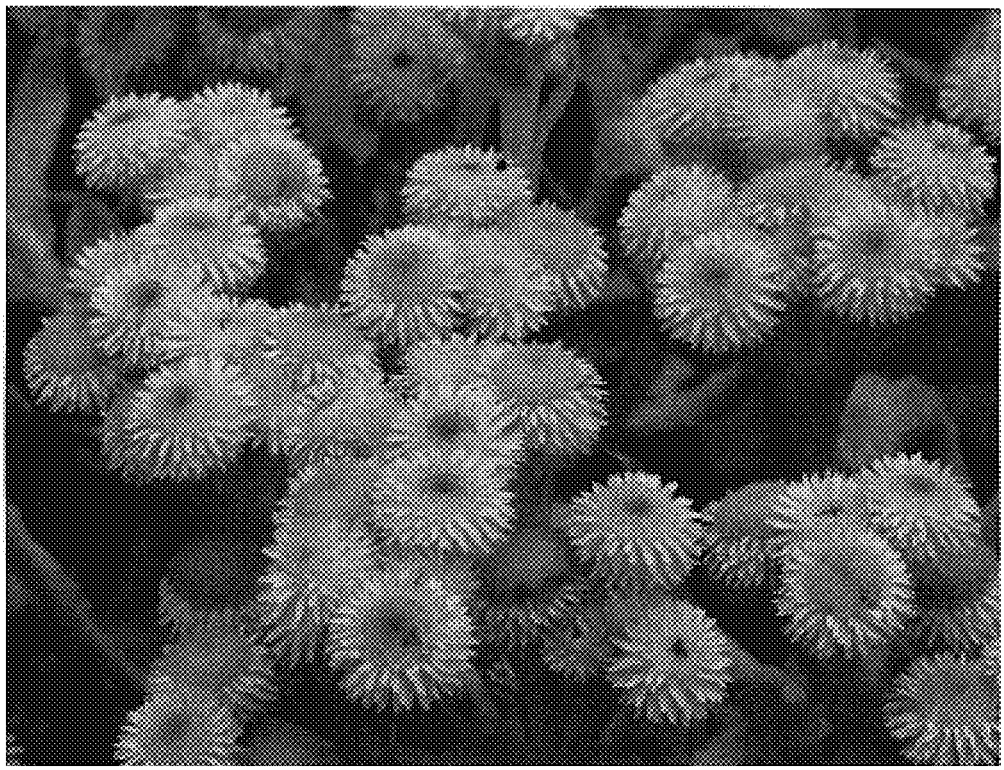

* * * * *